United States Patent
Swanson et al.

(10) Patent No.: US 6,704,105 B1
(45) Date of Patent: Mar. 9, 2004

(54) ELECTIVELY MAXIMIZING AND MINIMIZING THE SCATTERING AND ABSORPTION OF ELECTROMAGNETIC WAVES

(75) Inventors: Nancy L. Swanson, Newburg, MD (US); Barton D. Billard, Fredericksburg, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 101 days.

(21) Appl. No.: 09/909,172

(22) Filed: Jul. 18, 2001

(51) Int. Cl.⁷ ................................. G01N 15/02
(52) U.S. Cl. ................. 356/336; 356/342; 356/335; 356/337
(58) Field of Search ............... 356/336, 335, 356/337, 338, 339, 340, 341, 342, 343, 432, 436, 437, 438, 439, 441, 442, 243.1, 243.2; 73/865.5, 432.1; 250/573, 574, 575

(56) References Cited

U.S. PATENT DOCUMENTS

| 5,534,056 A | 7/1996 | Kuehnle et al. ............ 106/455 |
| 5,818,583 A | 10/1998 | Sevick-Muraca et al. ... 356/336 |
| 5,853,994 A | 12/1998 | Gopinathan et al. ........... 435/6 |
| 6,017,981 A | 1/2000 | Hugo ........................ 523/216 |

OTHER PUBLICATIONS

N. L. Swanson, D. B. Billard, "Multiple scattering efficiency and optical extinction", Phys. Rev. E, vol. 61, No. 4, Apr. 2000, pp. 4518–4522.*

N. L. Swanson, B. D. Billard, T. L. Gennaro, "Limits of optical transmission measurements with application to particle sizing techniques", Appl. Opt., vol. 38, No. 27, Sep. 20, 1999, pp. 5887–5893.*

* cited by examiner

*Primary Examiner*—Thong Nguyen
*Assistant Examiner*—Arnel C. Lavarias
(74) *Attorney, Agent, or Firm*—James B. Bechtel, Esq.; Matthew J. Bussan, Esq.; Auzville Jackson, Jr. Esq,

(57) ABSTRACT

A method for controlling both the scattering and absorption of electromagnetic waves. The method is based on prescribing the sizes of the particles that are suspended in a specified medium and a ratio of the refractive indices of the particles and the medium. This method can be used in applications that require maximizing or minimizing scattering of electromagnetic waves. The present method can also be used in applications that require maximizing or minimizing absorption of electromagnetic waves. Further, the invention provides control of backscattering (radar cross section) and, controlling any combination of scattering, absorption and backscattering of electromagnetic waves. Applications for the present method include stealth technology, friend or foe identification, and defensive screening.

9 Claims, 8 Drawing Sheets

ELECTIVELY MAXIMIZING AND MINIMIZING THE SCATTERING AND ABSORPTION OF ELECTROMAGNETIC WAVES

ORIGIN OF THE INVENTION

The invention described herein was made in the performance of official duties by employees of the Department of the Navy and may be manufactured, used, licensed by or for the Government for any governmental purpose without the payment of any royalty thereon.

FIELD OF THE INVENTION

The present invention relates generally to the field of electromagnetic waves and more specifically to a method for maximizing and minimizing the scattering and absorption of electromagnetic waves.

BACKGROUND OF THE INVENTION

When light strikes a material, it interacts with the atoms in the material, and the corresponding effects depend on the frequency of the light and the atomic structure of the material. In transparent materials, the electrons in the material oscillate, or vibrate, while the light is present. This oscillation momentarily takes energy away from the light and then puts it back again. The result is to slow down the light wave without leaving energy behind. Denser materials generally slow the light more than less dense materials, but the effect also depends on the frequency or wavelength of the light.

Materials that are not completely transparent either absorb light or reflect it. In absorbing materials, such as dark colored cloth, the energy of the oscillating electrons does not go back to the light. The energy instead goes toward increasing the motion of the atoms, which causes the material to heat up. The atoms in reflective materials, such as metals, re-radiate light that cancels out the original wave. Only the light re-radiated back out of the material is observed. All materials exhibit some degree of absorption, refraction, and reflection of light. The study of the behavior of light in materials and how to use this behavior to control light is called optics.

Refraction is the bending of light when it passes from one kind of material into another. Because light travels at a different speed in different materials, it must change speeds at the boundary between two materials. If a beam of light hits this boundary at an angle, then light on the side of the beam that hits first will be forced to slow down or speed up before light on the other side hits the new material. This makes the beam bend, or refract, at the boundary. Light bouncing off an object underwater, for instance, travels first through the water and then through the air to reach an observer's eye. From certain angles an object that is partially submerged appears bent where it enters the water because light from the part underwater is being refracted.

The refractive index of a material is the ratio of the speed of light in empty space to the speed of light inside the material. Because light of different frequencies travels at different speeds in a material, the refractive index is different for different frequencies. This means that light of different colors is bent by different angles as it passes from one material into another. This effect produces the familiar colorful spectrum seen when sunlight passes through a glass prism. The angle of bending at a boundary between two transparent materials is related to the refractive indices of the materials through Snell's Law, a mathematical formula that is used to design lenses and other optical devices to control light.

Reflection also occurs when light hits the boundary between two materials. Some of the light hitting the boundary will be reflected into the first material. If light strikes the boundary at an angle, the light is reflected at the same angle, similar to the way balls bounce when they hit the floor. Light that is reflected from a flat boundary, such as the boundary between air and a smooth lake, will form a mirror image. Light reflected from a curved surface may be focused into a point, a line, or onto an area, depending on the curvature of the surface.

Scattering occurs when the atoms of a transparent material are not smoothly distributed over distances greater than the length of a light wave, but are bunched up into lumps of molecules or particles. The sky is bright because molecules and particles in the air scatter sunlight. Light with higher frequencies and shorter wavelengths is scattered more than light with lower frequencies and longer wavelengths. The atmosphere scatters violet light the most, but human eyes do not see this color, or frequency, well. The eye responds well to blue, though, which is the next most scattered color. Sunsets look red because when the sun is at the horizon, sunlight has to travel through a longer distance of atmosphere to reach the eye. The thick layer of air, dust and haze scatters away much of the blue light.

The waves that accompany light are made up of oscillating, or vibrating, electric and magnetic fields, which are force fields that surround charged particles and influence other charged particles in their vicinity. These electric and magnetic fields change strength and direction at right angles, or perpendicularly, to each other in a plane. The electromagnetic wave formed by these fields travels in a direction perpendicular to the field's strength (coming out of the plane). The relationship between the fields and the wave formed can be understood by imagining a wave in a taut rope. Grasping the rope and moving it up and down simulates the action of a moving charge upon the electric field. It creates a wave that travels along the rope in a direction that is perpendicular to the initial up and down movement.

Because electromagnetic waves are transverse—that is, the vibration that creates them is perpendicular to the direction in which they travel, they are similar to waves on a rope or waves traveling on the surface of water. Unlike these waves, however, which require a rope or water, light does not need a medium, or substance, through which to travel. Light from the sun and distant stars reaches the earth by traveling through the vacuum of space. The waves associated with natural sources of light are irregular, like the water waves in a busy harbor. Such waves can be thought of as being made up of many smooth waves, where the motion is regular and the wave stretches out indefinitely with regularly spaced peaks and valleys. Such regular waves are called monochromatic because they correspond to a single color of light.

The wavelength of a monochromatic wave is the distance between two consecutive wave peaks. Wavelengths of visible light can be measured in meters or in nanometers (nm), which are one billionth of a meter. Frequency corresponds to the number of wavelengths that pass by a certain point in space in a given amount of time. This value is usually measured in cycles per second, or Hertz (Hz). All electromagnetic waves travel at the same speed, so in one second, more short waves will pass by a point in space than will long waves. This means that shorter waves have a higher frequency than longer waves. The relationship between wavelength, speed, and frequency is expressed by the equation: wave speed equals wavelength times frequency, or $$c = lf$$

where c is the speed of a light wave in m/sec ($3 \times 10^8$ m/sec in a vacuum), l is the wavelength in meters, and f is the wave's frequency in Hz.

The amplitude of an electromagnetic wave is the height of the wave, measured from a point midway between a peak and a trough to the peak of the wave. This height corresponds to the maximum strength of the electric and magnetic fields and to the number of photons in the light.

The electromagnetic spectrum refers to the entire range of frequencies or wavelengths of electromagnetic waves. Light traditionally refers to the range of frequencies that can be seen by humans. The frequencies of these waves are very high, about one-half to three-quarters of a million billion ($5 \times 10^{14}$ to $7.5 \times 10^{14}$) Hz. Their wavelengths range from 400 to 700 nm. X rays have wavelengths ranging from several thousandths of a nanometer to several nanometers, and radio waves have wavelengths ranging from several meters to several thousand meters.

A laser is a special kind of light source that produces very regular waves that permit the light to be very tightly focused. Laser is actually an acronym for Light Amplification by Stimulated Emission of Radiation. Each radiating charge in a non-laser light source produces a light wave that may be a little different from the waves produced by the other charges. Laser sources have atoms whose electrons radiate all in step, or synchronously. As a result, the electrons produce light that is polarized, monochromatic, and coherent, which means that its waves remain in step, with their peaks and troughs coinciding, over long distances.

This coherence is made possible by the phenomenon of stimulated emission. If an atom is immersed in a light wave with a frequency, polarization, and direction the same as light that the atom could emit, then the radiation already present stimulates the atom to emit more of the same, rather than emit a slightly different wave. So the existing light is amplified by the addition of one more photon from the atom. A luminescent light source can provide the initial amplification, and mirrors are used to continue the amplification. Lasers have many applications in medicine, scientific research, military technology, and communications. They provide a very focused, powerful, and controllable energy source that can be used to perform delicate tasks. Laser light can be used to drill holes in diamonds and to make microelectronic components. The precision of lasers helps doctors perform surgery without damaging the surrounding tissue. Lasers are useful for space communications because laser light can carry a great deal of information and travel long distances without losing signal strength.

The present invention provides a systematic prescription for selecting appropriate spherical particle size and properties, in conjunction with the properties of the medium in which the particles are to be suspended, for applications involving scattering and absorption of electromagnetic waves. The invention is applicable to a variety of applications where it is desirable to either maximize or minimize scattering and/or absorption of electromagnetic radiation. The following description treats the general case of maximized attenuation from scattering or absorption. The total scattering plus absorption is referred to hereinafter as attenuation.

SUMMARY OF THE INVENTION

The present invention is a method for maximizing or minimizing electromagnetic scattering and absorption. As such, it is applicable to the entire electromagnetic spectrum. The specific application in which the invention is used, such as stealth or identification applications, determines which procedures of a set of procedures, discussed further below, are applied. This systematic prescription allows investigation of many combinations of scattering materials and media via calculated predictions of scattering and absorption properties. A significant improvement over trial and error methods of measuring properties of material combinations results. Using this procedure, only those combinations found to be promising for the application need be obtained and measured if confirmation of the predictions is desired, thus saving time and expense.

BRIEF DESCRIPTION OF THE DRAWINGS

The invention of the present application will now be described in more detail with reference to the accompanying drawings, given only by way of example, in which.

DETAILED DESCRIPTION OF THE INVENTION

Figure 1:
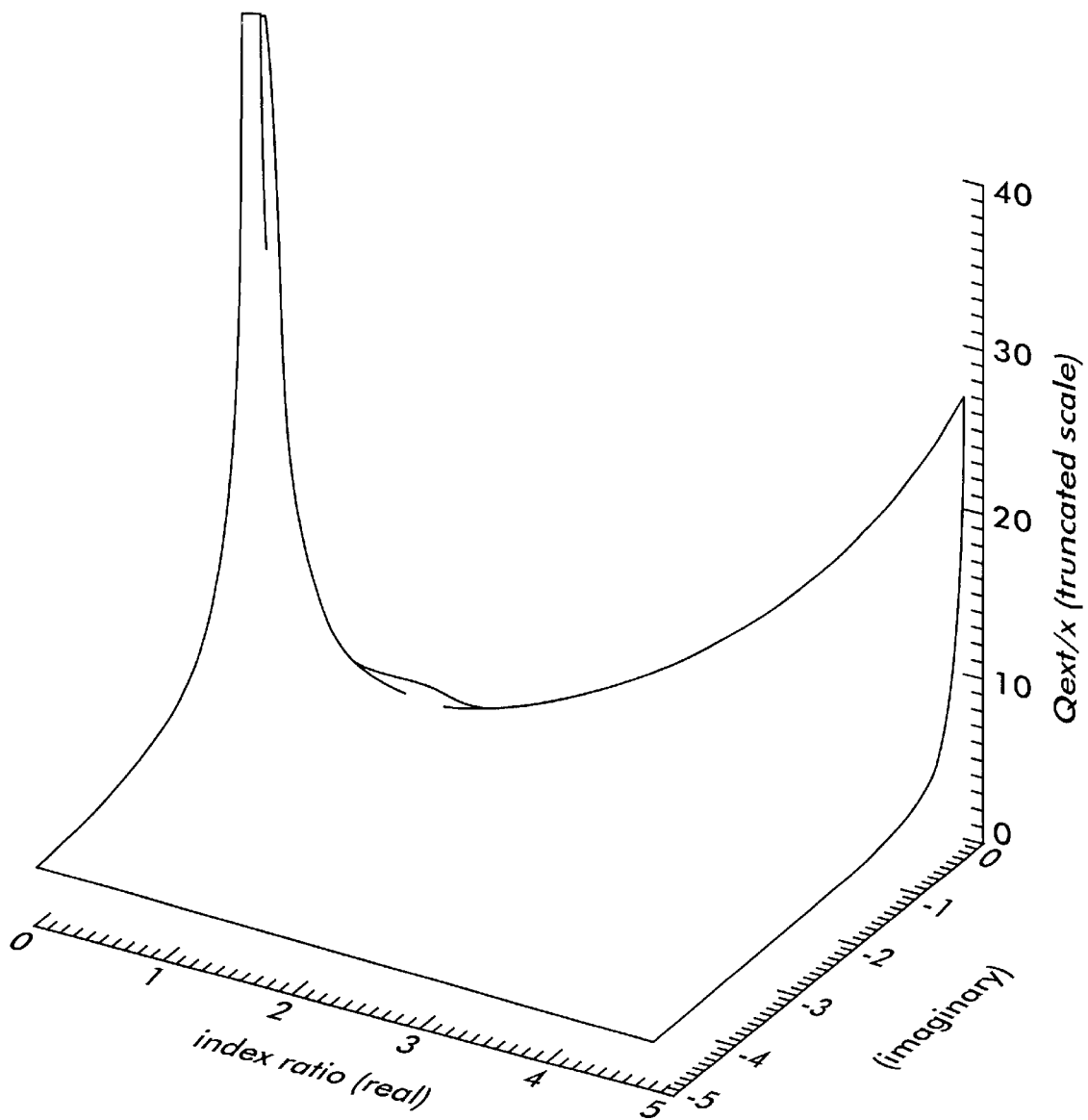
FIG. 1 shows a surface plot mapping the largest value of $Q_{ext}/x$ found for each value of the refractive index ratio on a grid in the complex plane.

The transmission of unscattered light can be related to the scattering efficiency, called the extinction Q, calculated from the Mie theory for single spheres. Further information on the Mie theory can be found in *Light Scattering by Small Particles*, by H. C. van de Hulst, Dover Publications Inc., N.Y. (1981) which is incorporated herein by reference. The intensity I(z) after transmission through a path length z in the medium is expressed in terms of the optical thickness $\tau$ by $$I(z) = I(0)e^{-\tau} \quad (1)$$

The optical thickness is the product of the path length z and the total attenuation $\xi$. The attenuation coefficient $\xi$ is the product of the total cross section $\sigma_T = \sigma_{scat} + \sigma_{abs}$ times the particle number density $\rho$. Thus $\tau$ can be written $$\tau = \xi z = \sigma_T \rho z \quad (2)$$

The extinction $Q_{ext} = Q_{scat} + Q_{abs}$ is the ratio of the total cross section to the geometric cross section $\sigma_{geo} = \pi r^2$ of the spheres $$Q_{ext} = \frac{\sigma_T}{\pi r^2} \quad (3)$$

The particle number density is related to the volume of a sphere and the volume ratio R, defined as the ratio of the volume occupied by the spheres to the total volume, thus $$R = \rho V_{sphere} = \rho 4/3 \pi r^3 \quad (4)$$

Equation (1) shows that a desired ratio of transmitted unattenuated light intensity I(z) to incident intensity I(0) is obtained by making the optical thickness of the scattering medium $\tau$ equal to the natural logarithm of this intensity ratio. Substitution from Equations (2) and (3) into Equation (4) gives the volume ratio $$R = \frac{4r\tau}{3zQ_{ext}} = \frac{2\lambda\tau}{3\pi z} \frac{X}{Q_{ext}} \quad (5)$$

In the second form on the right of Equation (5), $\lambda$ is the wavelength in the medium and the particle radius r has been expressed in terms of the size parameter X defined as $$X = \frac{2\pi r}{\lambda} \quad (6)$$

Equation (5) shows that one can minimize the volume ratio R of scattering spheres needed by minimizing the ratio of the size parameter X to the extinction $Q_{ext}$ with fixed z, $\tau$ and $\lambda$. Alternatively, given a maximum allowable volume ratio R of a coating, the optical thickness $\tau$ can be maximized. To maximize $\tau$, solve Equation (5) for $\tau$, which results in $$\tau = \frac{3\pi z R}{2\lambda} \frac{Q_{ext}}{X} \quad (7)$$

Thus, minimizing R is equivalent to maximizing the optical thickness $\tau$ for fixed path length z, wavelength $\lambda$, and R. When maximizing $\tau$, the quantity $3\pi zR/2\lambda$ is constant and results in a vertical shift in the plot of $\tau$ versus $Q_{ext}/X$. The constant will change the peak value but not the position along the x-axis. One may therefore set the constant equal to 1 and find the peak value and position for a number of refractive index ratios.

Figure 2:
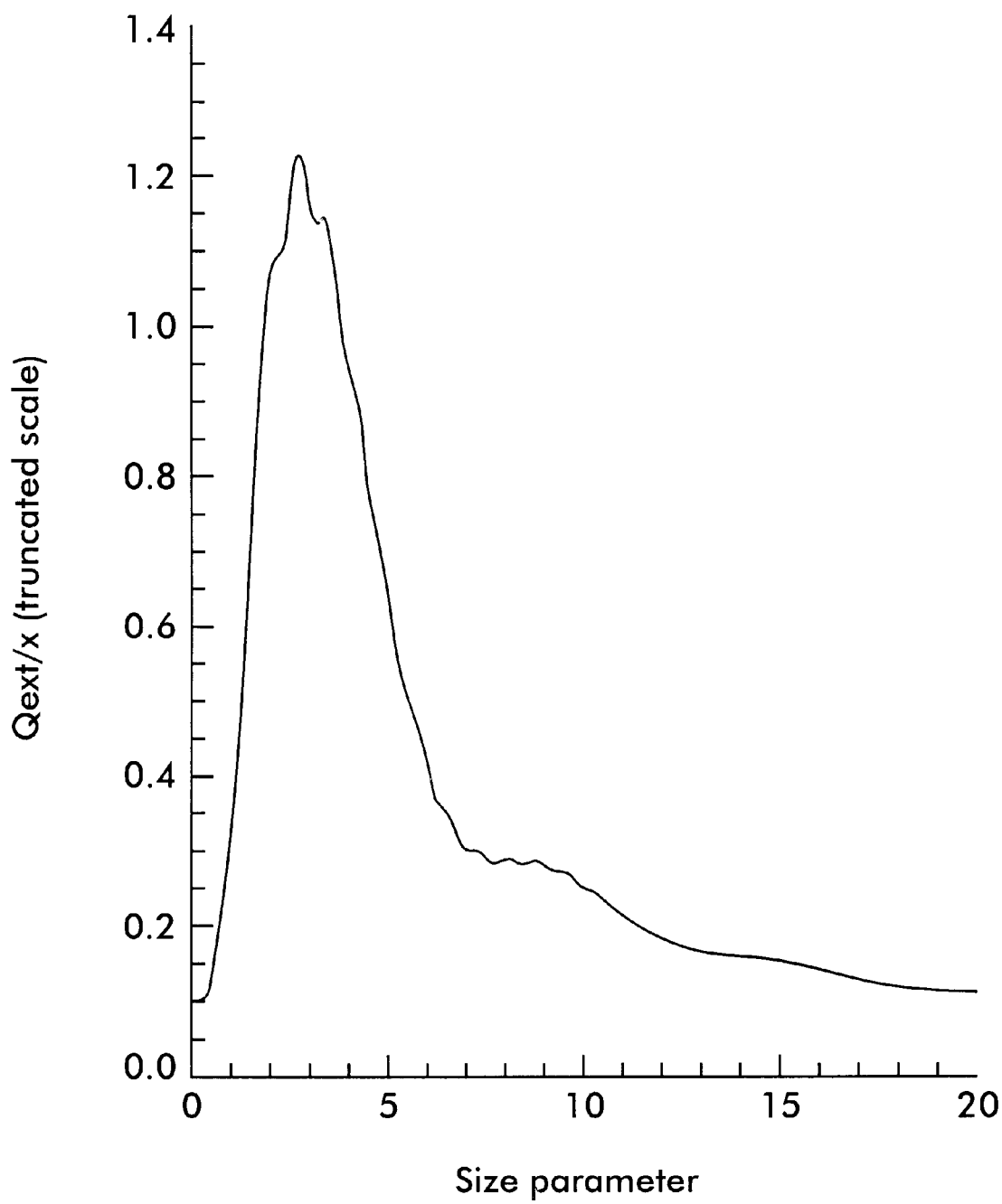
FIG. 2 is a sample plot of $Q_{ext}/x$ used to find the surface value for a grid point in FIG. 1.

Referring to FIG. 1, the Mie theory provides a way of calculating the extinction Q as a function of the size parameter X, given the ratio m of the refractive indices of the scattering particle and the medium. These calculations have been performed numerically for a range of values for m and X to create FIG. 1, which may be used in the selection process. FIG. 1 covers a range in the complex plane where we may search for combinations of the available scattering materials and media that have a desirable ratio m of refractive indices. For each value of m, the maximum of the ratio $Q_{ext}/X$ was determined as indicated with an example being shown in FIG. 2. The higher points on the resulting surface represent locations of desirable refractive index ratios for maximum scattering and/or absorption. The maximum for the curve in FIG. 2 is 1.2264 for a size parameter X of 2.65. The refractive index ratio for which the curve is calculated is the ratio for the grid point at 1.55–0.05i.

Figure 3:
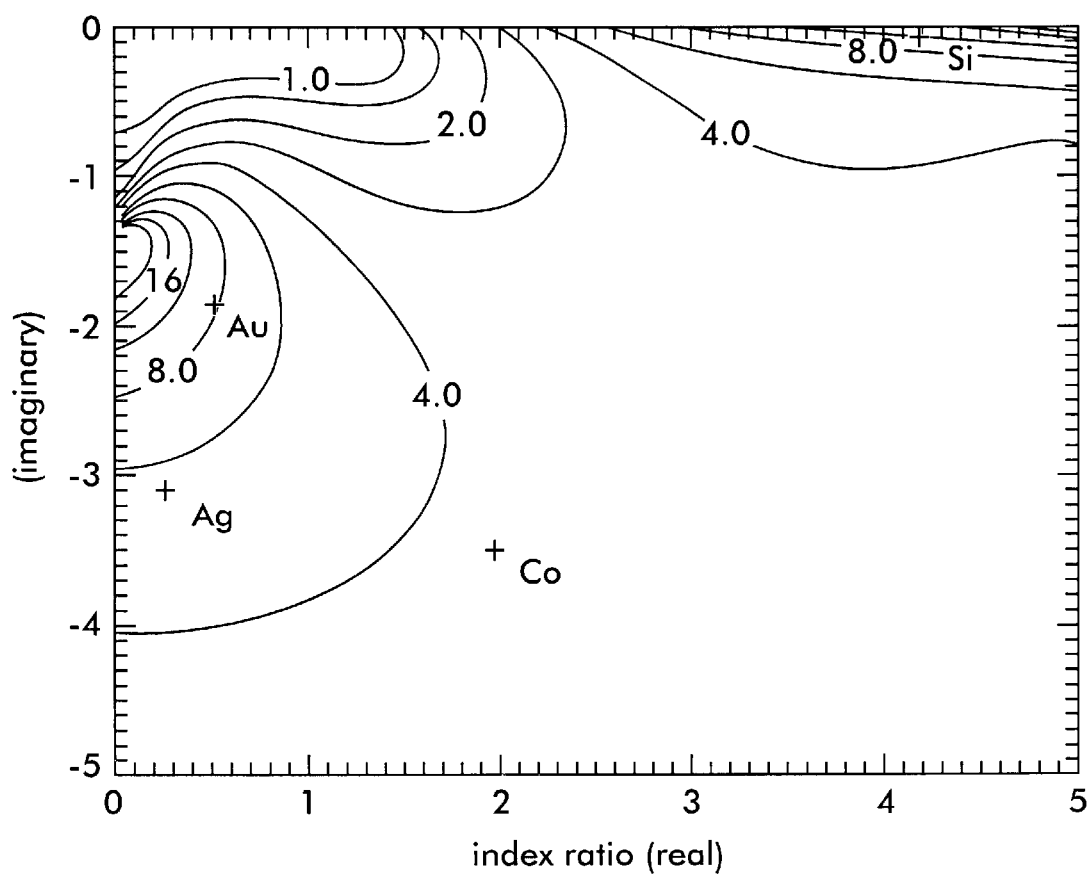
FIG. 3 shows a contour plot of the largest values of $Q_{ext}/x$ found for each value of the refractive index ratios on a grid in the complex plane.

With the wavelength(s) of operation and available materials identified, the refractive indices can be measured or looked up, and the ratios of possible combinations of scattering particles and media can be calculated and placed on a map. FIG. 3 shows the FIG. 1 map as a contour plot with values marked for various elements assuming air is the medium. Positions marked by the + symbol show the refractive index ratio for various elements. The positions shown are for a wavelength of 514.5 nanometers. If the application involves a range of wavelengths, the marks would be replaced by tracks representing the range of refractive index ratio for each material. For a different medium, the points would be shifted toward the origin by reducing the distance by the ratio of the index of air to that of the new medium. Examining this map allows selection of an efficient combination of medium and scattering particle type.

Figure 4:
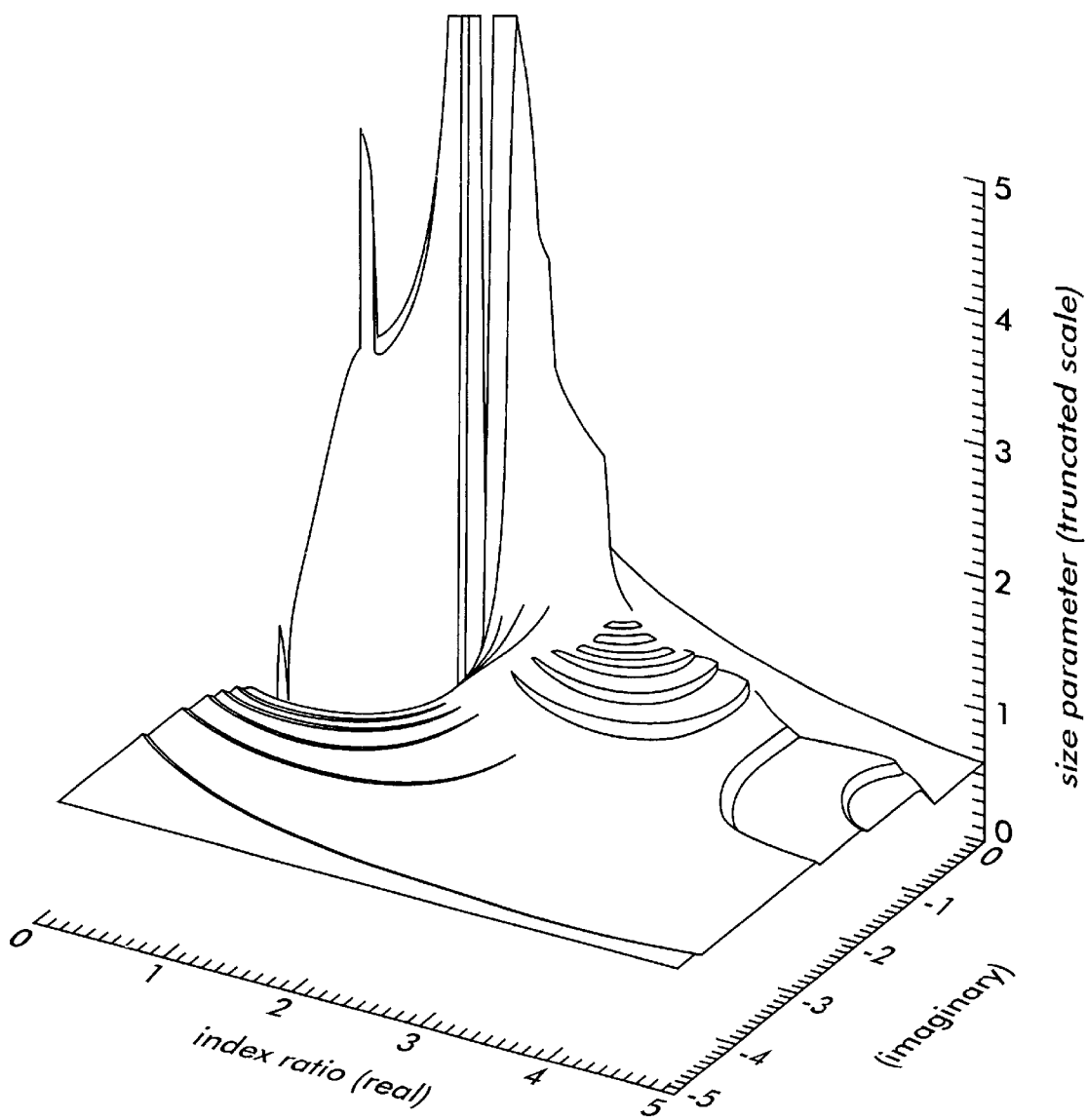
FIG. 4 shows the size parameter (x) values where the largest $Q_{ext}/x$ is found for each value of the refractive index ratios on a grid in the complex plane.

The size parameter needed is then obtained from the map of FIG. 4. In the map of FIG. 4, the height represents the size parameter x where the maximum was found. In the case of a range of wavelengths, a range of refractive index ratios for the combination of materials would be marked as segments of curves on the map. A steep slope of the surface along the track representing this range for the selected combination could indicate that a single particle size would not be suitable over the entire wavelength range. If R is sufficiently small over the wavelength range, more than one size or a size distribution could be used.

The specific procedures can be broken down into 6 categories:

c.1. Maximize Scattering;
c.2. Minimize Scattering;
c.3. Maximize Absorption;
c.4. Minimize Absorption;
c.5. Maximize Backscattering (radar cross section); and
c.6. Minimize Backscattering (radar cross section).

Most applications will require some combination of the above procedures. For example, stealth applications require low radar cross section or being undetectable by laser range finders would require a combination of c.1, c.3 and c.6. Providing markings to identify friend or foe would require a combination of c.2, c.4 and c.5. Designing a screen to defeat sophisticated low-light imaging equipment used for spying could be accomplished by selecting a combination of c.1, c.3 and c.5. The steps for each procedure of the above 6 categories are as follows.

c.1. Procedure for Maximizing Scattering

Step 1

Determine the wavelength (or wavelength range) of interest and potential materials for scattering particles and media.

Step 2

Obtain the refractive indices of potential scattering particle and scattering medium materials for the wavelength (or wavelength range) of the application. From these data, compute the refractive index ratios (scattering particle to medium) for the various combinations to be considered. The range of these index ratios will determine the range of the map needed.

Step 3

Figure 5:
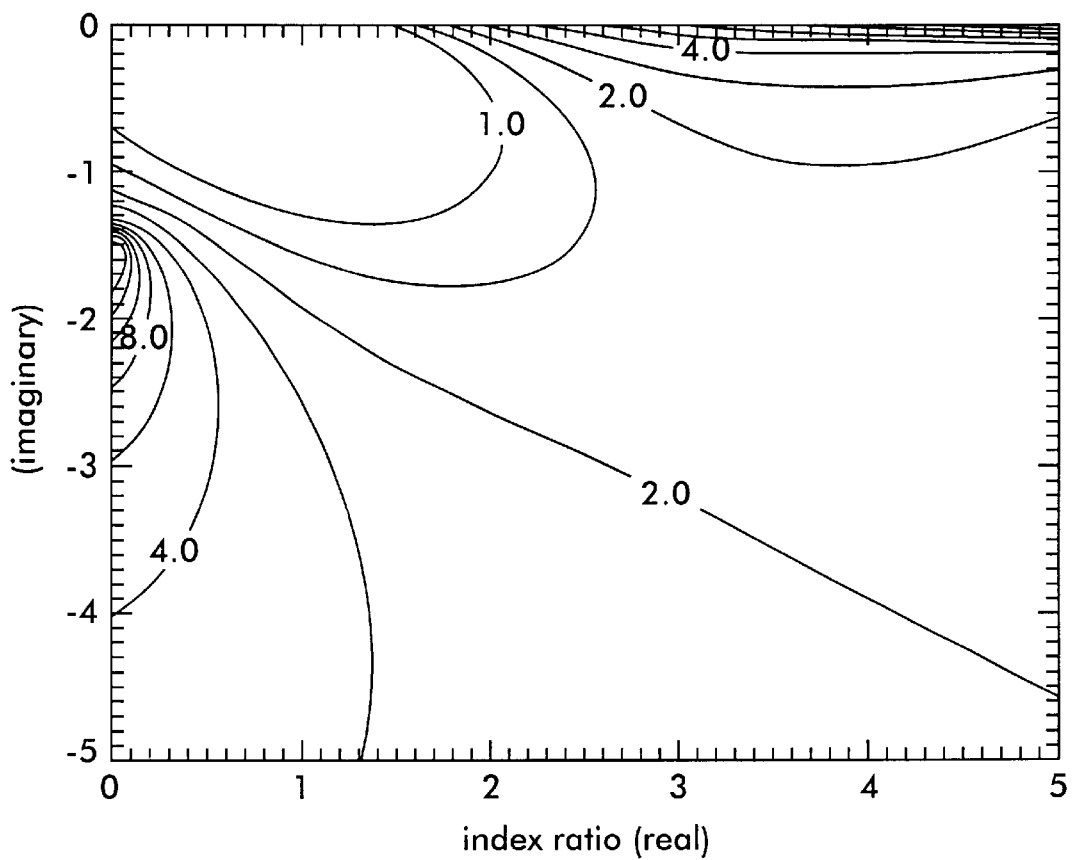
FIG. 5 is a contour plot of the largest values of $Q_{scat}/x$ found for each value of the refractive index ratios on a grid in the complex plane.

FIG. 5 shows an example of a map for evaluating the combinations of scattering particle to medium. It is constructed using Mie theory calculations similar to those used for FIG. 3. Divide the area of the complex plane covering the refractive index ratios of the combinations to be considered into a grid. Obtain Mie theory curves of $Q_{scat}$ versus X numerically for each refractive index ratio on the grid. The scattering extinction $Q_{scat}$ is defined as the cross section for scattering divided by the geometric cross section. Find the maximum of $Q_{scat}/X$. The value of this maximum [max $(Q_{scat}/X)$], along with the size parameter X where it occurs, is associated with the grid point. Repeat these calculations for each grid point.

Step 4

Construct a contour plot of max($Q_{scat}/X$) over the grid from the results of step 3 to produce a map like FIG. 5.

Step 5

For each combination of materials (i.e., scattering particle and medium), plot the complex refractive index ratio (i.e., a point for single wavelength or a curve for a wavelength range) on the map obtained in step 4. The optimum combination of materials falls inside the highest contour of $Q_{scat}/X$.

Step 6

For a single wavelength, it is now only necessary to find the particle size needed for the chosen combination of materials that fall into the highest contour of $Q_{scat}/X$. Use the Mie theory to obtain $Q_{scat}$ as a function of X for the exact refractive index ratio(s) of the chosen material combination (s). Plot the resulting curve of $Q_{scat}/X$ versus size parameter. Determine the size parameter X at which the maximum of $Q_{scat}/X$ occurs.

Step 6

To cover a wavelength range one must determine particle sizes for representative wavelengths in the range of interest. This is done as described in step 6a using values of the materials' complex refractive index ratio at the representative wavelengths. One must also confirm that the optimum size found for one wavelength is near enough to optimum at other wavelengths.

c.2. Procedure for Minimizing Scattering

This procedure assumes that this optimization is needed in combination with another optimization (most likely c.4 or c.5). The other optimization determines the initial choice of materials, the size, and volume ratio of scattering particles. Otherwise, eliminating particles minimizes scattering. This procedure provides a means of making the final selection among materials that satisfy the other criteria.

Step 1

Identify a set of possible material combinations, including particle types and sizes based on the other optimization criteria (e.g., c.4 or c.6).

Step 2

Calculate the scattering extinction $Q_{scat}$ for each prospective combination based on the refractive index ratio and size parameter of the combination at the representative wavelengths.

Step 3

Figure 6:
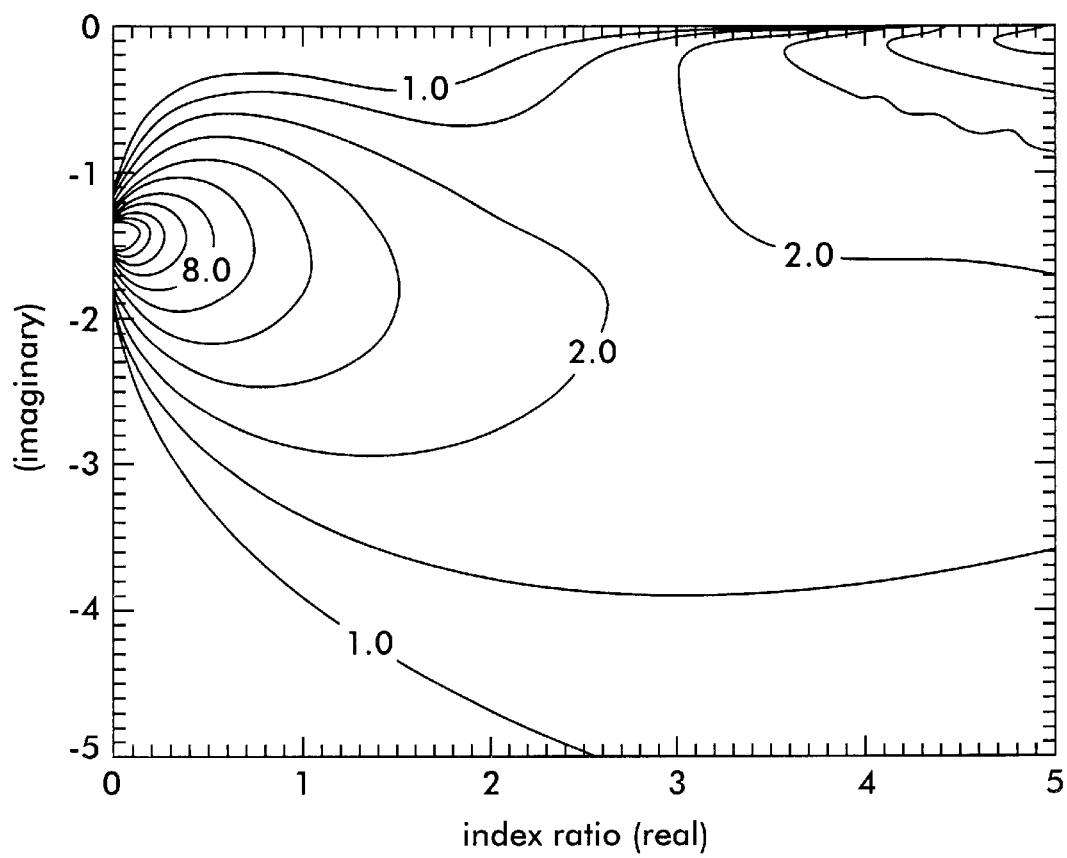
FIG. 6 is a contour plot of the largest values of $Q_{abs}/x$ found for each value of the refractive index ratios on a grid in the complex plane.

Divide the results of Step 2 for each combination by the size parameter and select the combination that gives the smallest $Q_{scat}/X$.

c.3. Procedure for Maximizing Absorption Follow procedure c.1, but substitute $Q_{abs}$ for $Q_{scat}$. $Q_{abs}$ is the ratio of the absorption cross section to the geometric cross section. FIG. 6 shows the map of max($Q_{abs}/x$) found for each value of the refractive index ratios on a grid in the complex plane, as would be used in this procedure.

c.4. Procedure for Minimizing Absorption

This procedure assumes that this optimization is used in combination with another optimization (most likely c.1 or c.2, and c.5) that partially determines the choice of materials, the size, and volume ratio of scattering particles. Otherwise, eliminating absorbing particles minimizes absorption. This procedure provides a means of making the final selection among materials that satisfy the other criteria.

To execute this procedure, follow c.2 but substitute $Q_{abs}$ for $Q_{scat}$.

c.5. Procedure for Maximizing Backscatter

Equations (1) and (2) together give $$I(z)=I(0)e^{-\rho\sigma z} \qquad (8)$$

for the light that reaches the plane at z without being scattered or absorbed. The rest of the light, I(z)-I(0), is scattered or absorbed along the way. A fraction of this light returns in the direction from which it came. The light that was reversed at z' somewhere between 0 and z is given by $$I_b(z) = \frac{I(0)\sigma_b}{\sigma}(1 - e^{-\rho\sigma z}) \qquad (9)$$

where $\sigma_b$ is the backscattering cross section given by the magnitude squared of the scattering phase function at $\pi$ radians. Applying Equation (8), a fraction $e^{-\rho\sigma z'}$ of the light that backscatters at a depth z' makes it back to z=0 without being scattered again or absorbed. Considering only a single backscatter event per photon, the total amount of backscattered at 180 degrees is $$I_b = \int_0^z dz' e^{-\rho\sigma z} \frac{dI_b(z')}{dz'} \qquad (10)$$

Substitution from Equation (9) results in $$I_b = \frac{I(0)\sigma_b}{\sigma}(1 - e^{-2\rho\sigma z}) \qquad (11)$$

Equation (11) is an underestimate, but if $\sigma_b$ is small compared to $\sigma$, the intensity increase resulting from the one or more additional pairs of backscatter events needed to add to the intensity calculated should be negligible. Equation (11) shows that the backscattering can be maximized when $\tau=\rho\sigma z$ is large $(1-e^{-2\rho\sigma z} \to 1)$ and $\sigma_b/\sigma$ is maximized. The following is obtained from the Mie theory $$\frac{\sigma_b}{\sigma_{geom}} = \frac{|s_1(\pi)|^2 \Omega}{\pi x^2} \qquad (12)$$

where $s_1(\pi)$ is the scattering matrix element evaluated at $\pi$, and $\Omega$ is the solid angle subtended by the receiver. The derivation of Equation (12) is valid if the scattering matrix element $s_1(\theta)$ does not vary much from $s_1(\pi)$ over the solid angle $\Omega$. Combining Equation (3) with Equation (12) results in $$\frac{\sigma_b}{\Omega\sigma} = \frac{4|s_1(\pi)|^2}{Q_{ext} x^2} \qquad (13)$$

Figure 7:
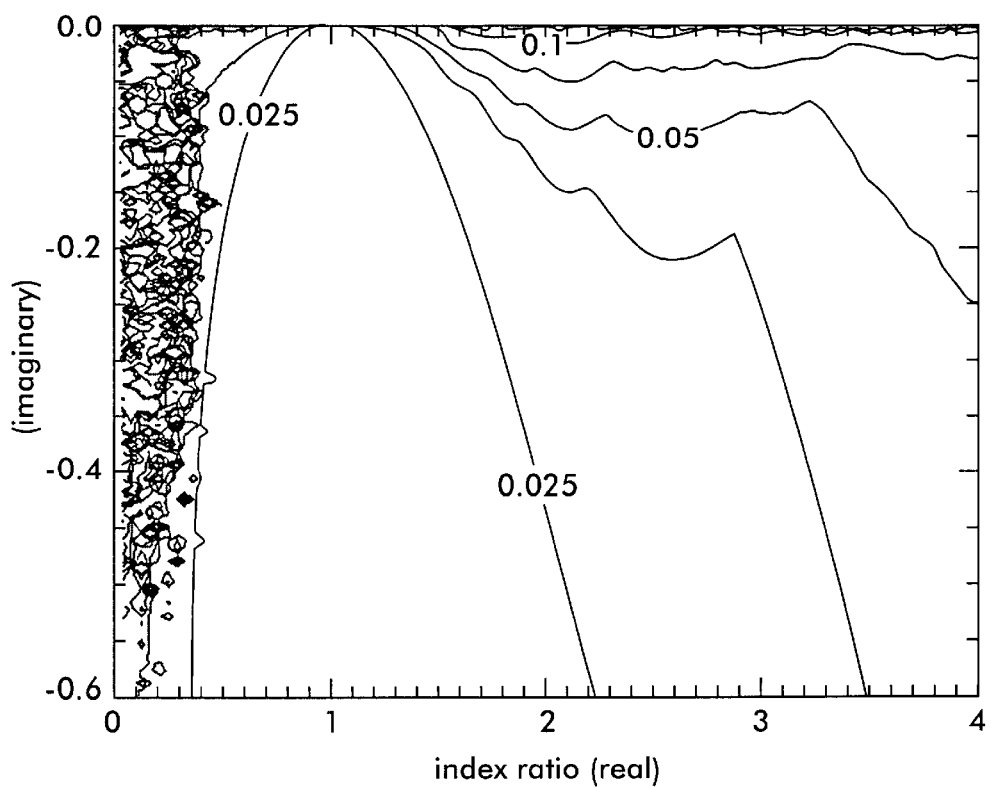
FIG. 7 shows a contour plot of the largest values of $\sigma_b/\Omega\sigma$ or found for each value of the refractive index ratios on a grid in the complex plane.
Figure 8:
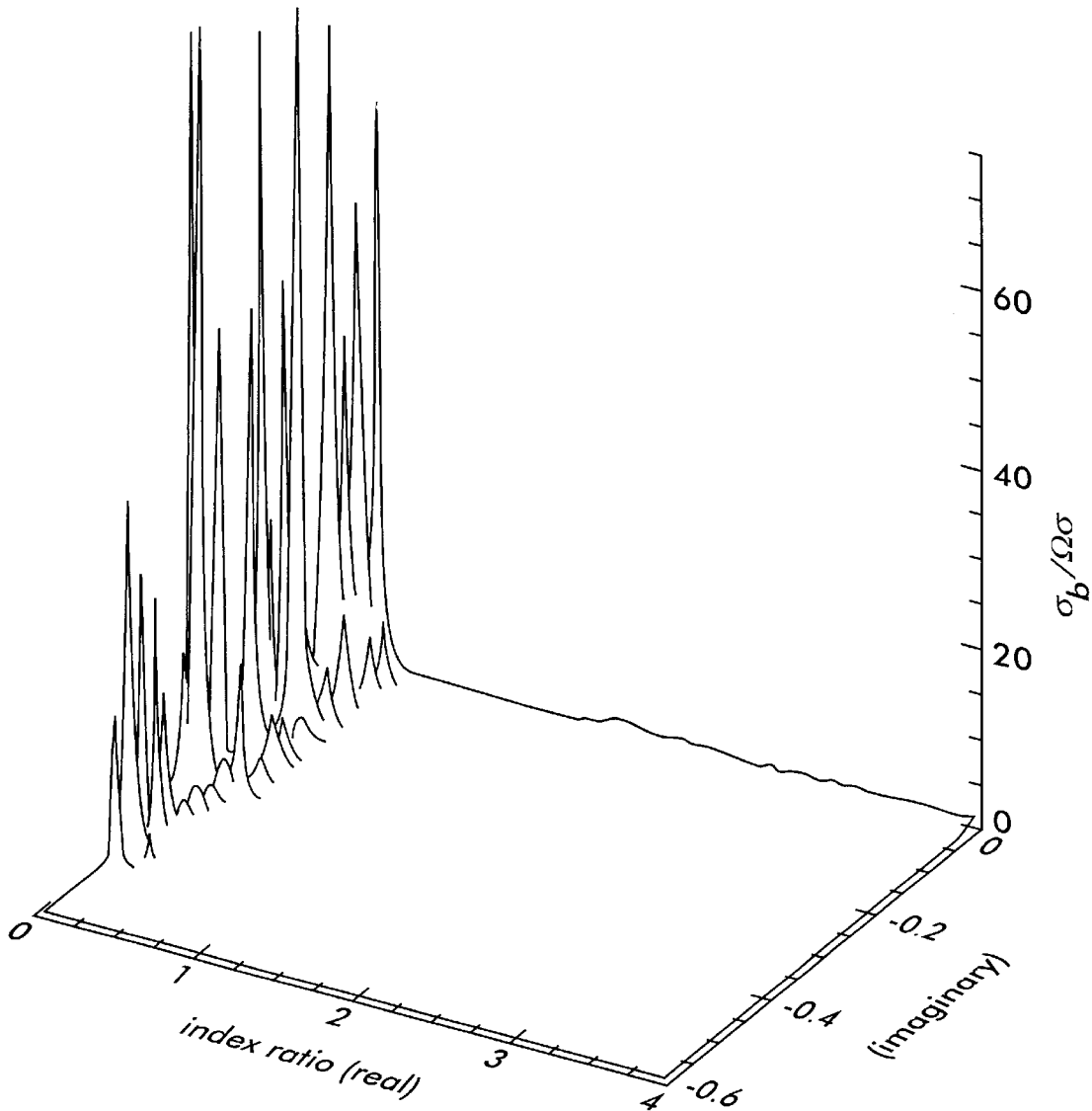
FIG. 8 is a surface plot of the largest values of $\sigma_b/\Omega\sigma$ found for each value of the refractive index ratios on a grid in the complex plane.

The quantities $s_1(\pi)$ and $Q_{ext}$ are generated from the Mie theory as functions of X. Maximize the ratio $\sigma_b/\Omega\sigma$ given in Equation (13), using the same procedure as outlined in c.1. FIGS. 7 and 8 show examples of contour and surface plots, respectively, of max($\sigma_b/\Omega\sigma$) used to optimize backscatter.

c.6. Procedure for Minimizing Backscatter

This procedure assumes that this optimization is used in combination with another optimization (most likely c.1 or c.3) that primarily determines the choice of materials, size, and volume ratio of scattering particles. Otherwise eliminating particles minimizes backscattering. This procedure provides a means of making the final selection among materials that satisfy the other criteria. Identify the prospective combinations from other requirements, and then check the backscatter for the chosen particle types and sizes. Select the combination that gives the smallest $\sigma_b/\Omega\sigma$.

The above systematic prescription allows investigation of many combinations of scattering materials and media via calculated prediction of scattering and absorption properties. A significant improvement over trial and error methods of measuring properties of material combinations results. Using this procedure, only those combinations found to be promising for the application need be obtained and measured if confirmation of the predictions is desired, thus saving time and expense.

It is not necessary to rely entirely on the maps constructed from Mie calculations on a rectangular grid of values of the complex refractive index ratio. At some point the possible combinations of media and scattering particle types may be sufficiently limited to allow consideration only of their specific refractive index ratios. One may list all the values for the combinations being considered and perform the Mie calculations for those ratios. Using the maximization of scattering procedure c.1 for example, one would calculate the curves of $Q_{scat}/X$ for each refractive index ratio and compare their maxima. This approach can be useful where the number of possible combinations of materials has already been limited in some way, or where distributions of particles are to be used. In the latter case the map can be used initially, then the Mie calculations for specific refractive index ratios can be carried out for the size distribution required, without having to recreate the entire map.

The foregoing description of the specific embodiments will so fully reveal the general nature of the invention that others can, by applying current knowledge, readily modify and/or adapt for various applications such specific embodiments without departing from the generic concept. Therefore, such adaptations and modifications should and are intended to be comprehended within the meaning and range of equivalents of the disclosed embodiments. It is to be understood that the phraseology of terminology employed herein is for the purpose of description and not of limitation.

We claim:

1. A method for maximizing scattering of electromagnetic waves incident upon a material that contains particles suspended in a medium, comprising the steps of:
    determining the wavelength or range of wavelengths of the electromagnetic waves;
    obtaining refractive indices of potential particles and mediums;
    computing refractive index ratios of particles to mediums for combinations of particles and mediums;
    dividing a complex plane covering the refractive index ratios into a grid;
    calculating Mie theory curves of scattering extinction versus particle size for each refractive index ratio on the grid;
    finding the maximum value of scattering extinction divided by particle size for each grid point;
    constructing a contour plot of the maximum values over the grid to produce a three dimensional map; and,
    plotting complex refractive index ratios, as a point for a single wavelength or as a curve for a wavelength range, on the map, wherein combinations of particles and medium that provide maximum scattering are found within the highest contours of the map, wherein backscattering of the electromagnetic waves is maximized.

2. A method for maximizing scattering of electromagnetic waves incident upon a material that contains particles suspended in a medium, comprising the steps of:
    determining the wavelength or range of wavelengths of the electromagnetic waves;
    obtaining refractive indices of potential particles and mediums;
    computing refractive index ratios of particles to mediums for combinations of particles and mediums;
    dividing a complex plane covering the refractive index ratios into a grid;
    calculating Mie theory curves of scattering extinction versus particle size for each refractive index ratio on the grid;
    finding the maximum value of scattering extinction divided by particle size for each grid point;
    constructing a contour plot of the maximum values over the grid to produce a three dimensional map; and,
    plotting complex refractive index ratios, as a point for a single wavelength or as a curve for a wavelength range, on the map, wherein combinations of particles and medium that provide maximum scattering are found within the highest contours of the map, wherein the particles and medium of the material are selected so as to also maximize absorption and minimize backscatter of the electromagnetic waves, thereby making the material a good choice for stealth type applications.

3. A method for maximizing scattering of electromagnetic waves incident upon a material that contains particles suspended in a medium, comprising the steps of:
    determining the wavelength or range of wavelengths of the electromagnetic waves;
    obtaining refractive indices of potential particles and mediums;
    computing refractive index ratios of particles to mediums for combinations of particles and mediums;
    dividing a complex plane covering the refractive index ratios into a grid;
    calculating Mie theory curves of scattering extinction versus particle size for each refractive index ratio on the grid;
    finding the maximum value of scattering extinction divided by particle size for each grid point;
    constructing a contour plot of the maximum values over the grid to produce a three dimensional map; and,
    plotting complex refractive index ratios, as a point for a single wavelength or as a curve for a wavelength range, on the map, wherein combinations of particles and medium that provide maximum scattering are found within the highest contours of the map, wherein the particles and medium of the material are selected so as to also maximize absorption and maximize backscatter of the electromagnetic waves, thereby making the material a good choice for a screen that defends against detection by low light imaging equipment.

4. A material that contains particles that are suspended in a medium, wherein the material selectively provides maximum scattering, backscattering and absorption of electromagnetic waves of a specified wavelength or wavelengths, depending upon a refractive index ratio between the particles and the medium.

5. The material of claim 4, wherein the particles and medium are selected so as to alternatively minimize scattering, backscattering and absorption of electromagnetic waves of a specified wavelength or wavelengths, based upon a relationship between the particles and the medium.

6. The material of claim 4, wherein the particles are spheres.

7. A material containing particles that are suspended in a medium, wherein the material selectively provides minimum scattering, backscattering and absorption of electromagnetic waves of a specified wavelength or wavelengths, based upon a refractive index ratio between the particles and the medium.

8. The material of claim 7, wherein the particles and medium are selected so as to alternatively maximize scattering, backscattering and absorption of electromagnetic waves of a specified wavelength or wavelengths, based upon a relationship between the particles and the medium.

9. The material of claim 7, wherein the particles are spheres.

* * * * *